United States Patent [19]
Barker et al.

[11] Patent Number: 5,652,142
[45] Date of Patent: *Jul. 29, 1997

[54] CELL CULTURE INSERT

[75] Inventors: Susan Barker, Tenafly; I-Hsi Chu, West Orange; Oresta N. Fedun, Wanaque; Tadeusz A. Tyndorf, Manalapan, all of N.J.

[73] Assignee: Becton, Dickinson and Company, Franklin Lakes, N.J.

[ * ] Notice: The term of this patent shall not extend beyond the expiration date of Pat. No. 5,366,893.

[21] Appl. No.: 535,368

[22] Filed: Sep. 28, 1995

Related U.S. Application Data

[63] Continuation of Ser. No. 952,113, Sep. 28, 1992, abandoned.

[51] Int. Cl.$^6$ ............................................ C12M 3/06
[52] U.S. Cl. .............................. 435/297.1; 435/297.5; 435/305.1; 422/101; 422/102; 422/104
[58] Field of Search ................ 435/297.5, 288.3, 435/288.4, 288.5, 297.1, 305.1, 305.2, 305.4; 422/101, 102; 210/238, 249, 250, 321.84, 460, 463, 476, 477

[56] References Cited

U.S. PATENT DOCUMENTS

| | | | |
|---|---|---|---|
| 2,677,646 | 5/1954 | Lovell et al. | 195/139 |
| 4,125,436 | 11/1978 | Liner | 195/127 |
| 4,246,339 | 1/1981 | Cole et al. | 435/7 |
| 4,308,351 | 12/1981 | Leighton et al. | 435/284 |
| 4,608,342 | 8/1986 | Nees | 435/240 |
| 4,670,396 | 6/1987 | Bear et al. | 435/285 |
| 4,686,190 | 8/1987 | Cramer et al. | 435/291 |
| 4,748,124 | 5/1988 | Vogler | 435/240 |
| 4,871,674 | 10/1989 | Matsui et al. | 435/284 |
| 4,917,793 | 4/1990 | Pitt et al. | 435/284 X |
| 4,975,377 | 12/1990 | Key | 422/102 X |
| 5,026,649 | 6/1991 | Lyman et al. | 435/284 |
| 5,139,951 | 8/1992 | Butz et al. | 435/297.5 |
| 5,215,920 | 6/1993 | Lyman et al. | 422/102 X |
| 5,366,893 | 11/1994 | Stevens et al. | 435/297.5 |

FOREIGN PATENT DOCUMENTS 0 495 213   12/1990   European Pat. Off. .

*Primary Examiner*—Jeffrey Snay
*Attorney, Agent, or Firm*—Nanette S. Thomas

[57] ABSTRACT

Apparatus for growing cells or tissue in vitro, which permits a concentration gradient of nutrients to develop through a permeable membrane to which a sample of tissue is attached. The permeable membrane is attached to the bottom end of a cell culture insert that in turn is supported by a flange connected to its upper end on the top of a well containing the nutrients. Restricted movement of the cell culture insert in the well may be facilitated by projections extending off the outer wall surface of the insert so as to avoid capillary action in the space between the well and the insert.

7 Claims, 4 Drawing Sheets

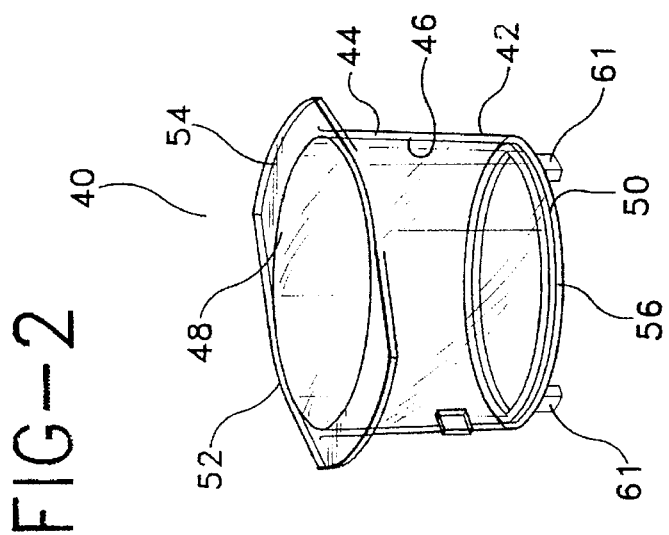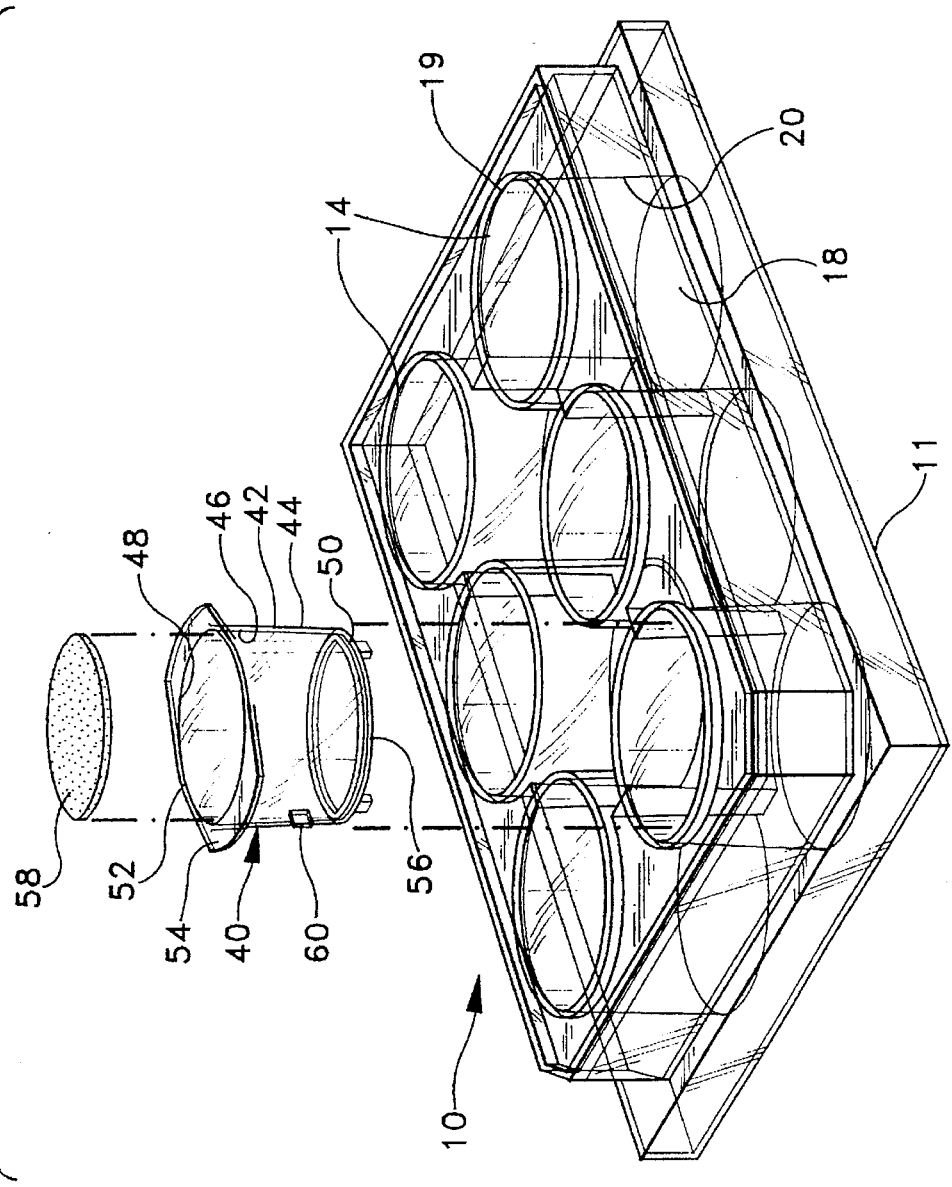

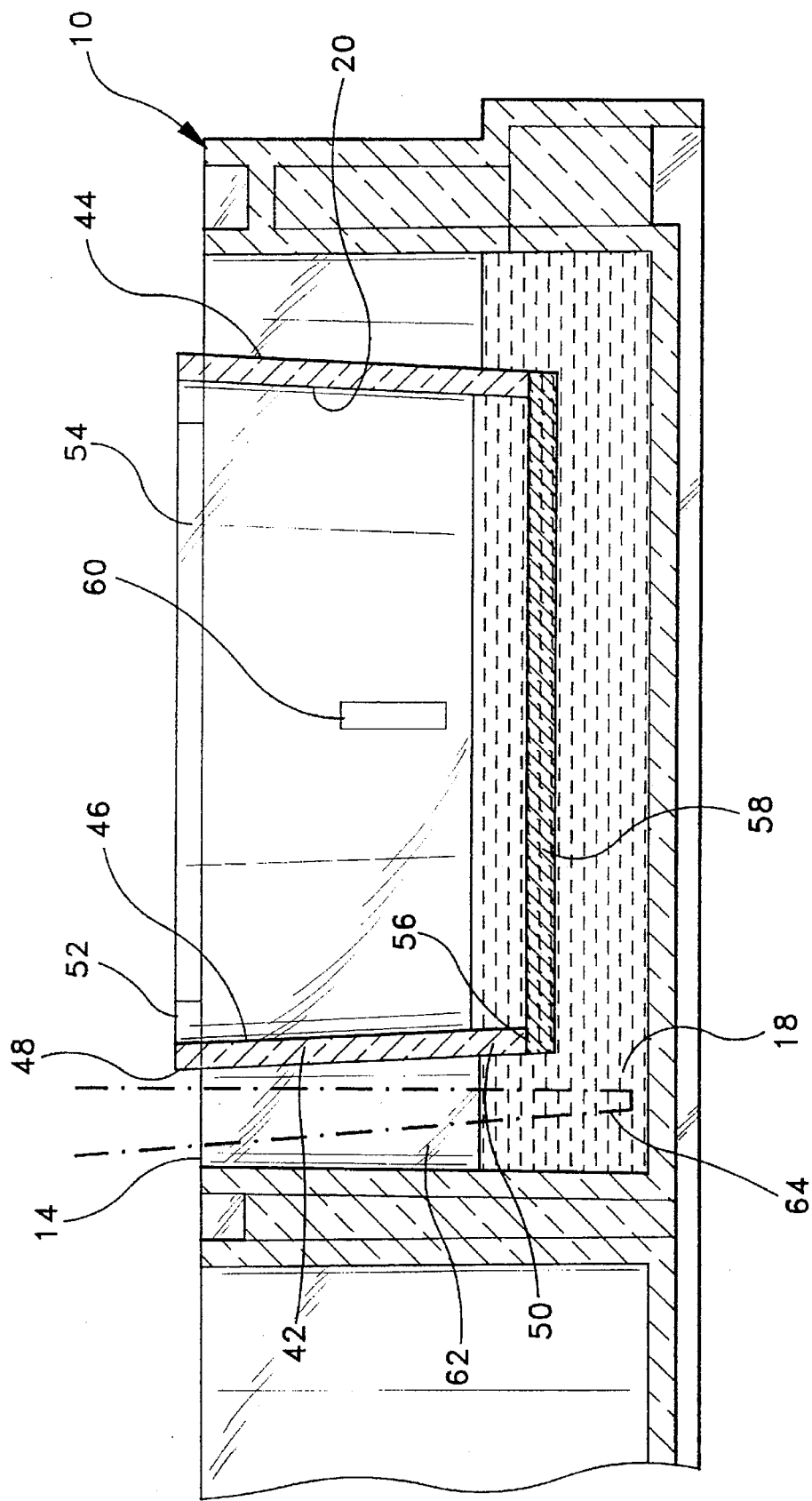

CELL CULTURE INSERT

This is a continuation of application Ser. No. 07/952,113, filed on Sep. 28, 1992, now abandoned.

BACKGROUND OF THE INVENTION

1. Field of the Invention

This invention relates to an apparatus for growing cells or tissue culture in vitro and more particularly comprises a new and improved cell culture insert for supporting tissue cultures in a fluid medium containing nutrients which promote the tissue culture growth.

2. Description of the Related Art

Cell culture inserts comprise a plastic material with a membrane on the bottom surface thereof so that there is free diffusion and transport of ions and macro-molecules. With the use of a suspended microporous membrane, two cell types, for example, can be cultured, one on each side of the membrane in the same well. Without suspension, cells on the bottom surface of the membrane would be exposed to damage. The microporous membrane allows free passage of macromolecules, proteins and ions. As a result, the interactions of the two cell types can be studied without actual physical contact between the two cell populations in the suspended state of the insert.

Conventional cell culture inserts and devices are described in U.S. Pat. Nos. 4,871,674 and 5,026,649. U.S. Pat. No. 4,871,674 discloses a cell culture insert which comprises discontinuous projecting parts for hanging the cell culture insert provided on an upper circumferential part. U.S. Pat. No. 5,026,649 discloses a cell culture insert which comprises a projecting part for hanging the culture cell which is provided over the whole upper circumferential part, with openings in the sidewalls for exchanging gas and for pipeting sample.

In the use of these cell culture inserts, gases may not be exchanged sufficiently because the area between the sidewall of the insert and the culture plate is too small. Furthermore, as descried in U.S. Pat. No. 5,026,649, portions of the cell culture insert could possibly become contaminated because openings are provided in the sidewall of the cell culture insert.

SUMMARY OF THE INVENTION

The present invention is a cell culture insert comprising a sidewall bordered by a top end surface and a bottom end surface wherein the bottom end surface has attached thereto a flat permeable membrane, a glass cover slip or the like. The top end surface of the insert carries at least one outwardly extending flange which serves to support the insert in the well of a tissue culture vessel. The geometric configuration of the insert is desirably a continuous circumference, however, any geometric configuration such as but not limited to, round, sphere, circle, oval, rectangle, square, octagon and the like may be used. In addition, the sidewall of the cell culture insert may taper from the top end to the bottom end.

Desirably, there at least two outwardly extending flanges on the top end surface of the cell culture insert. These flanges may be spaced along the top end surface of the cell culture insert.

The exterior dimensions of the portion of the cell culture insert within the well of a tissue culture vessel are sufficiently less than the well interior diameter to allow a pipet or similar device to be positioned between the tissue culture vessel and the cell culture insert for fluid filling or aspiration. The space allows the pipet to reach the bottom of the vessel and introduce or remove medium from beneath the membrane and about the outer surface of the sidewall of the cell culture insert without contaminating the upper surface of the membrane.

Preferably, the outer surface of the sidewall of the cell culture insert includes means for restricting or preventing the flange of the cell culture insert from falling into the well of the tissue culture vessel. The flange may shift from excess movement of the cell culture insert within the well. Such movement of the cell culture insert within the well facilitates pipet access. The movement can be limited in one axis by the means for restricting or preventing the flange of the cell culture insert from falling into the well. The movement of the cell culture insert, however, may be such that the cell culture insert wall and the substantially parallel well interior wall can touch at one or more locations.

The cell culture insert may further comprise at least one support footing on the bottom end surface of the cell culture insert. The footing provides a degree of clearance between the membrane and the well bottom of the tissue culture vessel in the event the outwardly extending flange is not compatible with the tissue culture vessel and cannot support the cell culture insert. Most preferably there are at least two support footings on the bottom end surface of the cell culture insert.

The cell culture insert of the present invention may be sized to be used with a multi-well tissue culture vessel having wells of a specific size. The cell culture insert may be made in different sizes and geometric configurations so as to be used with different sizes and geometric configured tissue culture vessels, such as but not limited to plates, dishes and the like.

An important feature of the cell culture insert of the present invention is the means for preventing or restricting the outer surface of the cell culture insert sidewall from moving close to the inner wall of the well of the tissue culture vessel in which it is placed so that capillary action of the fluid in the well is minimized.

An additional feature of the present invention is that a pipet may be inserted between the outer surface sidewall of the cell culture insert and the inner wall of the tissue culture vessel in which the cell culture insert is placed. The pipet may be inserted without disturbing or removing the cell culture insert from the well of the tissue culture vessel so that fluid may be introduced to or removed from the space beneath the membrane of the cell culture insert and from the bottom of the well of the tissue culture vessel.

A further feature of the cell culture insert of the present invention is that it may be supported in a tissue culture vessel with flanges so that there is clearance between the bottom of the membrane and the bottom of the well of the tissue culture vessel. The degree of clearance allows the fluid in the tissue culture vessel to substantially achieve a controlled static head and diffusion so that cells may be properly cultured on the bottom surface of the membrane. In addition, the feet may support the cell culture insert when it is removed from the tissue culture vessel and placed on a flat surface,

DESCRIPTION OF THE DRAWINGS

FIG. 1 is an exploded perspective view of a tissue culture vessel and cell culture insert.

FIG. 2 is an enlarged perspective view of the cell culture insert of the present invention without the membrane.

FIG. 6 is a cross-sectional view taken along lines 6—6 of FIG. 4 illustrating where a pipet tip may enter the space between the cell culture insert and the well of the tissue culture vessel.

DETAILED DESCRIPTION

Figure 4:
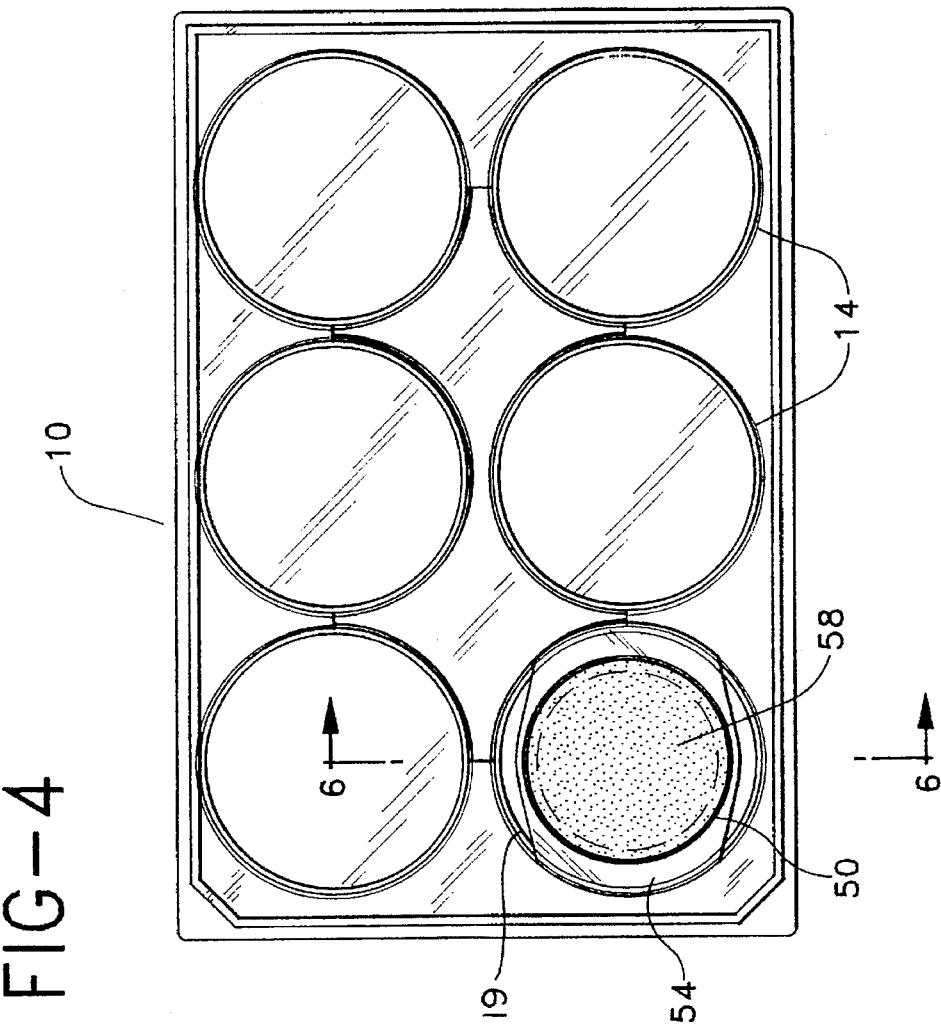
FIG. 4 is a top view of FIG. 1 illustrating the cell culture insert supported in the well of a tissue culture vessel.

The apparatus for growing tissue cultures as shown in FIG. 1 includes a culture vessel 10 and a cell culture insert 40. Although only a six well culture vessel is shown, it should be appreciated that the culture vessel may have eight, twelve, twenty-four or some other number of wells selected for the particular purpose for which the apparatus is used.

Culture vessel 10 includes a base 11 comprising a number of wells 14 each comprising a sidewall 20 closed at the bottom by a wall 18 and open at the top end 19. Base 11 typically is transparent and may be molded, for example, of polyvinylchloride.

While in the foregoing paragraphs, the details of the culture vessel illustrated are described, it is to be appreciated that the vessel itself does not form part of the present invention, and the cell culture insert of the present invention may be sized to fit and be used with other culture vessels.

Figure 3:
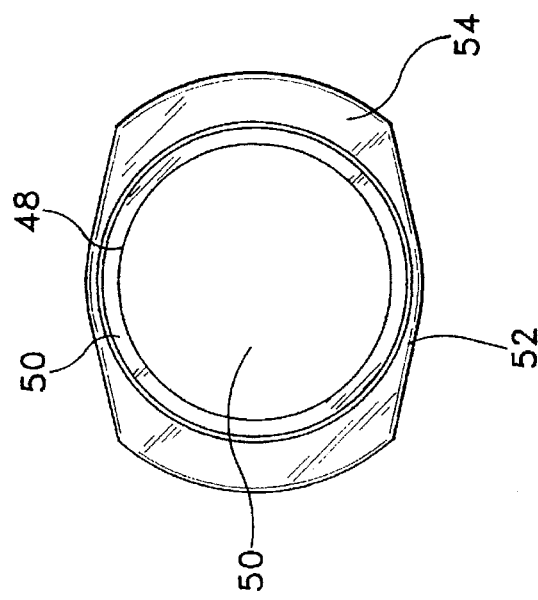
FIG. 3 is a top view of FIG. 2.

FIGS. 2 and 3 further illustrate cell culture insert 40 of the present invention comprising a body wall 42 having an outer wall surface 44 and inner wall surface 46. Body wall 42 extends from an upper portion 48 to a lower portion 50. The body wall may taper from the upper portion to the lower portion.

Upper portion 48 comprises a top surface 52 which carries an outwardly extending flange 54 which provides support to the insert when placed in the well of a culture vessel. Preferably, flange 50 comprises a horizontal orientation for resting on the top of the well of the culture vessel. Lower portion 50 comprises a bottom surface 56 to which a microporous membrane 58 may be adhered. The membrane may be made of suitable material including, but not limited to, perforated inert film, hydrated gel, or a layered combination.

On outer wall surface 44 of the insert is located at least one projecting or extending tab 60. Projecting tab 60 provides stability to the insert and prevents or restricts the flange from falling into the well of the culture vessel. The flange may shift from excess movement of the cell culture insert within the well. Movement of the cell culture insert within the well facilitates pipet access in the space between the outer wall surface of the insert and the sidewall of the well. Projecting tab 60 may limit the movement of the cell culture insert in one axis. The movement of the cell culture insert, however, may be such that the cell culture outer wall surface and the sidewall of the well can touch at one or more locations. The projecting tabs can be any geometric configuration. Most preferably, the projecting tabs may be located on the outer wall surface about half way between the top surface and the bottom surface, although this location is not critical to the invention.

Figure 5:
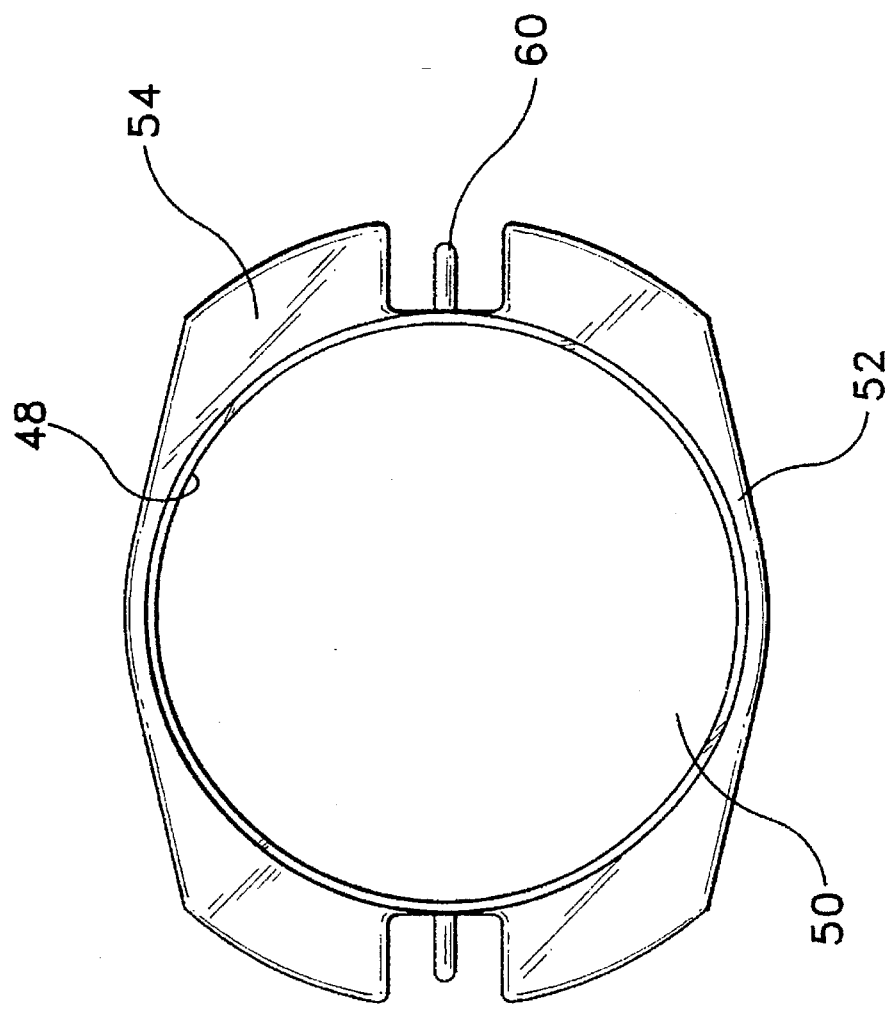
FIG. 5 is an alternate top view of the cell culture insert of FIG. 2 wherein the outwardly extending flange is formed with an opening for pipetting or for facilitating placement and removal of the cell culture insert in a tissue culture vessel.

As shown in FIGS. 2, 3, 4 and 5 when more than one outwardly extending flange 54 is used, they are spaced to allow for insertion of probes or pipets during the culturing procedure. The configuration of flange may be structured to fit most situations. As shown in FIG. 5 flange 54 may be formed with an opening for inserting a piper or probe in the space between the outer wall of the insert and the well. The flange configuration may facilitate the aseptic placement and removal of the cell culture insert into or out of the well of the culture vessel with tweezers or forceps, and allow for air circulation to minimize compartmentalization as well as providing support to the cell culture insert when placed in the well of a culture vessel.

It is most desirable that a space be maintained between the membrane on the bottom surface of the insert and the well of the culture vessel so that cells may be cultured on both sides of the membrane. Therefore, the cell culture insert of the present invention may further include feet or supports 61 located on the bottom surface of the cell culture insert. Feet 61 may be used when the extending flanges may not provide adequate support of the insert in a particular culture vessel arrangement. Feet 61 may further provide adequate support to the cell culture insert when placed on a flat surface.

FIG. 6 illustrates the insert as supported in culture vessel 10 and where a pipet tip 64 may enter the space between outer wall surface 44 of the cell culture insert and sidewall 20 of the culture vessel. Further shown are the projecting tabs 60 which may prevent or restrict the flange of the insert from falling into the well of the culture vessel.

It will be appreciated that when cell culture insert 40 is set within well 14 and spaced sufficiently from the well sidewall 20 as facilitated by projecting tabs 60, no capillary action will occur to cause solution or media in space 62 from wicking up outer surface 44 and entering the interior of the insert or spilling from well 14. Furthermore, because flange 54 supports the device, the culture may be treated if desired in a deeper well than suggested so as to provide more solution beneath the membrane. While it is customary to position the membrane a distance above bottom wall 18 if desired, a well of greater depth may be used so as to provide additional space between the membrane and bottom wall 18.

As practitioners-in-the-art will understand, the cell inserts of the present invention may be comprised of simple moldable parts which can be mass produced from a variety of materials, including, for example, polyethylene, polystyrene, polyethylene terephthalate, and polypropylene.

What is claimed is:

1. A cell culture insert comprising:
   a hollow chamber comprising a top surface, a bottom surface, a sidewall comprising an inner and outer surface extending from said top surface to said bottom surface, a porous membrane aligned with said bottom surface, at least two separate, flanges extending radially outward from said top surface beyond said sidewall and a projection extending radially outward from said outer surface of said sidewall spaced away from said flange, said top surface and said bottom surface and not adjacent said flange or said top surface, wherein said flanges comprise an opening.

2. The insert of claim 1 further comprising means for supporting said insert on said bottom surface.

3. The insert of claim 1 wherein said sidewall tapers from said top surface to said bottom surface.

4. A cell culture insert comprising:
   a hollow chamber comprising a top surface, a bottom surface, a sidewall comprising an inner and outer surface extending from said top surface to said bottom surface, a porous membrane aligned with said bottom surface, a plurality of discontinuous projecting flanges having an opening, and means for restricting movement of said cell culture insert and extending from said outer surface of said sidewall spaced away from said plurality of discontinuous projecting flanges, said top surface and said bottom surface and not adjacent said flanges or said top surface, wherein said flanges comprise an opening.

5. The insert of claim 4 wherein said means for restricting movement of said insert is at least one projecting tab.

6. Apparatus for use in growing tissue cultures in vitro comprising:

a tissue culture vessel having a well with inner and bottom walls for receiving media; and a cell culture insert in said well comprising a top surface, a bottom surface, a sidewall comprising an inner and outer surface and extending from said top surface to said bottom surface, a permeable membrane attached to said bottom surface, at least two separate flanges extending from said top surface, and means for restricting movement of said cell culture insert in said well of said tissue culture vessel extending from said outer surface of said sidewall spaced away from said top surface and said bottom surface and not adjacent said flanges or said top surface, wherein said flanges comprise an opening.

7. The insert of claim 6 wherein said means for restricting movement of said insert is at least one projecting tab.

* * * * *